US008454673B2

(12) United States Patent
Al-Marashi et al.

(10) Patent No.: US 8,454,673 B2
(45) Date of Patent: Jun. 4, 2013

(54) RAPID-EXCHANGE BALLOON CATHETER SHAFT AND METHOD

(75) Inventors: Laila Al-Marashi, Mountain View, CA (US); David Grewe, Glen Gardner, NJ (US); Stephen Griffin, San Jose, CA (US); Elaine Lim, Fremont, CA (US); David Majercak, Stewartsville, NJ (US); Roger Stevens, San Jose, CA (US)

(73) Assignee: Cordis Corporation, Bridgewater, NJ (US)

( * ) Notice: Subject to any disclaimer, the term of this patent is extended or adjusted under 35 U.S.C. 154(b) by 98 days.

(21) Appl. No.: 12/906,976

(22) Filed: Oct. 18, 2010

(65) Prior Publication Data

US 2011/0034989 A1 Feb. 10, 2011

Related U.S. Application Data

(63) Continuation of application No. 12/008,509, filed on Jan. 11, 2008, now Pat. No. 7,815,600, which is a continuation-in-part of application No. 10/691,823, filed on Oct. 23, 2003, now Pat. No. 7,520,863, which is a continuation-in-part of application No. 10/224,168, filed on Aug. 20, 2002, now Pat. No. 7,128,718.

(60) Provisional application No. 60/930,471, filed on May 16, 2007, provisional application No. 60/880,000, filed on Jan. 11, 2007, provisional application No. 60/366,739, filed on Mar. 22, 2002.

(51) Int. Cl.
*A61F 2/84* (2006.01)

(52) U.S. Cl.
USPC .................................. 623/1.11; 604/101.02

(58) Field of Classification Search
CPC ........................................................ A61F 2/84
USPC .......... 604/101.02, 103.01–103.04; 606/192; 623/1.12–1.17, 1.2
See application file for complete search history.

(56) References Cited

U.S. PATENT DOCUMENTS

| 4,003,369 A | 1/1977 | Heilman et al. |
| 4,665,906 A | 5/1987 | Jervis |

(Continued)

FOREIGN PATENT DOCUMENTS

| EP | 1611914 A1 | 1/2006 |
| WO | WO 03/051446 A1 | 6/2003 |
| WO | WO 2006/107919 A1 | 10/2006 |

OTHER PUBLICATIONS

European Supplementary European Search Report mailed on Feb. 28, 2011 from corresponding EP08705569.

*Primary Examiner* — Manuel Mendez
*Assistant Examiner* — Gerald Landry, II

(57) ABSTRACT

A balloon catheter or stent delivery system for medical treatment of a patient has a proximal hub, a balloon, and an improved shaft design. The catheter shaft has a rapid-exchange configuration, and a tubular outer body that includes a hypotube extending from the catheter proximal end to a position at or near a proximal leg of the balloon. An inner tubular body defines a guidewire lumen extending from a distal guidewire port at the catheter distal end to a proximal port located at a position between the balloon and the hub. A distal leg of the balloon is directly or indirectly affixed to the inner body, and a proximal leg of the balloon is affixed to the distal end of the outer body. The hypotube has an aperture for accepting the inner body proximal end, and a circumferential cut pattern. The cut pattern adds flexibility, and may extend from the hypotube distal end to a position proximal of the proximal guidewire port. The cut pattern may have any desired shape, including a spiral, a helical undulating path, or an overlapping serpentine path with inflection points, for example. The hypotube has a fluid-tight covering such as a heat-shrink polymer, so the outer body supports pressure of an inflation medium. The proximal guidewire port may be positioned on or between the individual portions of the cut pattern, or at a position beyond the cut pattern.

14 Claims, 7 Drawing Sheets

U.S. PATENT DOCUMENTS

| | | |
|---|---|---|
| 4,719,924 A | 1/1988 | Crittenden et al. |
| 4,757,827 A | 7/1988 | Buchbinder et al. |
| 4,763,647 A | 8/1988 | Gambale |
| 4,770,188 A | 9/1988 | Chikama |
| 4,813,434 A | 3/1989 | Buchbinder et al. |
| 4,815,478 A | 3/1989 | Buchbinder et al. |
| 4,827,941 A | 5/1989 | Taylor et al. |
| 4,854,325 A | 8/1989 | Stevens |
| 4,875,489 A | 10/1989 | Messner et al. |
| 4,881,981 A | 11/1989 | Thoma et al. |
| 4,886,067 A | 12/1989 | Palermo |
| 4,921,482 A | 5/1990 | Hammerslag et al. |
| 4,923,462 A | 5/1990 | Stevens |
| 4,925,445 A | 5/1990 | Sakamoto et al. |
| 4,935,088 A | 6/1990 | Mitsuyama |
| 4,936,845 A | 6/1990 | Stevens |
| 4,940,062 A | 7/1990 | Hampton et al. |
| 4,953,553 A | 9/1990 | Tremulis |
| 4,966,163 A | 10/1990 | Kra et al. |
| 4,984,581 A | 1/1991 | Stice |
| 4,998,916 A | 3/1991 | Hammerslag et al. |
| 5,037,391 A | 8/1991 | Hammerslag et al. |
| 5,190,050 A | 3/1993 | Nitzsche |
| 5,203,772 A | 4/1993 | Hammerslag et al. |
| 5,242,394 A | 9/1993 | Tremulis |
| 5,341,818 A | 8/1994 | Abrams et al. |
| 5,365,942 A | 11/1994 | Shank |
| 5,368,049 A | 11/1994 | Raman et al. |
| 5,372,587 A | 12/1994 | Hammerslag et al. |
| 5,397,305 A | 3/1995 | Kawula et al. |
| 5,480,382 A | 1/1996 | Hammerslag et al. |
| 5,501,694 A | 3/1996 | Ressemann et al. |
| 5,695,111 A | 12/1997 | Nanis et al. |
| 5,807,279 A | 9/1998 | Viera |
| 5,813,997 A | 9/1998 | Imran et al. |
| 5,882,333 A | 3/1999 | Schaer et al. |
| 5,891,055 A | 4/1999 | Sauter |
| 5,908,405 A | 6/1999 | Imran et al. |
| 5,931,830 A | 8/1999 | Jacobsen et al. |
| 5,944,689 A * | 8/1999 | Houser et al. .............. 604/95.04 |
| 6,027,460 A | 2/2000 | Shturman |
| 6,027,863 A | 2/2000 | Donadio, III |
| 6,048,338 A | 4/2000 | Larson et al. |
| 6,059,739 A | 5/2000 | Baumann |
| 6,126,649 A | 10/2000 | VanTassel et al. |
| 6,146,338 A | 11/2000 | Gardeski et al. |
| 6,193,706 B1 | 2/2001 | Thorud et al. |
| 6,273,876 B1 | 8/2001 | Klima et al. |
| 6,306,105 B1 | 10/2001 | Rooney et al. |
| 6,352,515 B1 | 3/2002 | Anderson et al. |
| 6,355,016 B1 | 3/2002 | Bagaoisan et al. |
| 6,375,628 B1 | 4/2002 | Zadno-Azizi et al. |
| 6,379,369 B1 | 4/2002 | Abrams et al. |
| 6,387,075 B1 | 5/2002 | Stivland et al. |
| 6,416,529 B1 * | 7/2002 | Holman et al. ................ 606/194 |
| 6,468,230 B2 | 10/2002 | Muni et al. |
| 6,475,209 B1 * | 11/2002 | Larson et al. ................. 604/525 |
| 6,488,637 B1 | 12/2002 | Eder et al. |
| 6,585,717 B1 * | 7/2003 | Wittenberger et al. ....... 604/523 |
| 7,166,100 B2 | 1/2007 | Jordan et al. |
| 2002/0019599 A1 | 2/2002 | Rooney et al. |
| 2002/0049392 A1 | 4/2002 | DeMello |
| 2002/0151966 A1 | 10/2002 | Eder et al. |
| 2002/0165534 A1 | 11/2002 | Hayzelden et al. |
| 2004/0243143 A1 | 12/2004 | Corcoran et al. |
| 2005/0059957 A1* | 3/2005 | Campbell et al. ............. 604/524 |
| 2005/0070847 A1 | 3/2005 | van Erp et al. |
| 2005/0131445 A1* | 6/2005 | Holman et al. ................ 606/194 |
| 2005/0283221 A1 | 12/2005 | Mann et al. |
| 2005/0288628 A1* | 12/2005 | Jordan et al. ................ 604/96.01 |
| 2007/0073331 A1* | 3/2007 | Brown et al. ................. 606/194 |
| 2007/0088323 A1* | 4/2007 | Campbell et al. ............. 604/523 |
| 2007/0142903 A1* | 6/2007 | Dave .............................. 623/1.22 |
| 2007/0219612 A1* | 9/2007 | Andreas et al. .............. 623/1.11 |

* cited by examiner

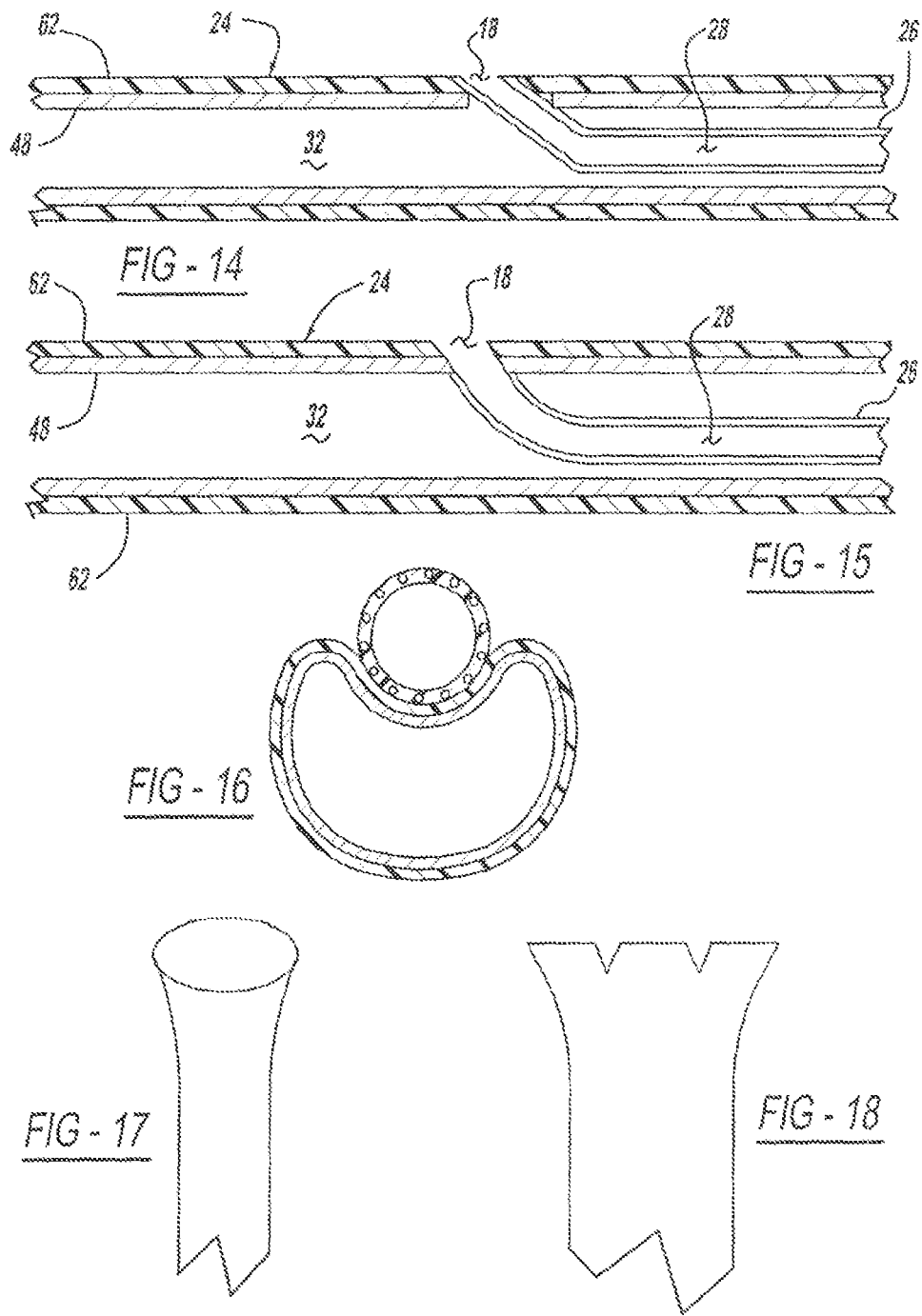

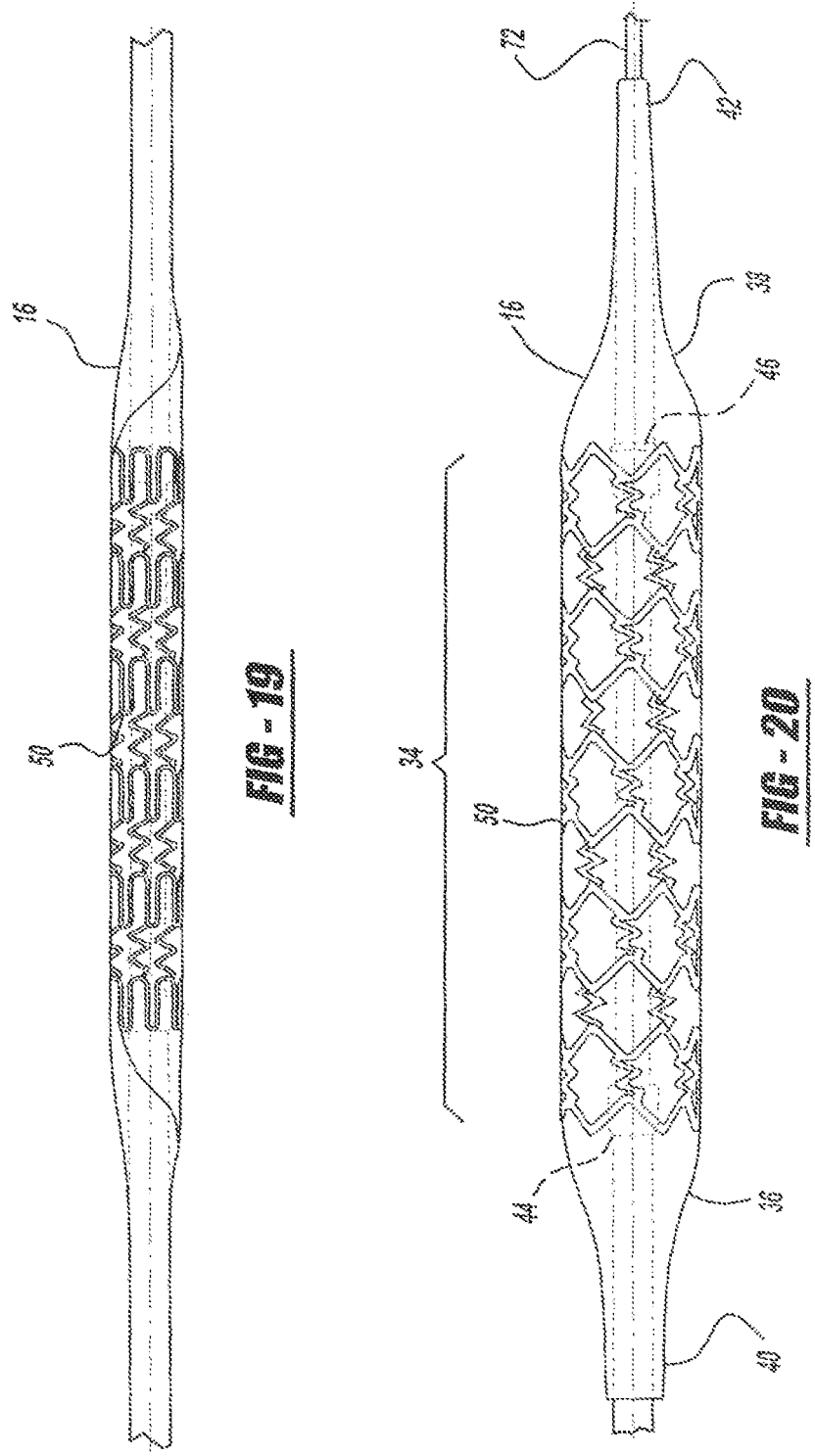

RAPID-EXCHANGE BALLOON CATHETER SHAFT AND METHOD

CROSS-REFERENCE TO RELATED APPLICATION

This application is a continuation and claims the benefit of priority under 35 USC §120 to U.S. patent application Ser. No. 12/008,509 filed on Jan. 11, 2008, which claims priority from U.S. Provisional Application No. 60/930,471, filed on May 16, 2007, and U.S. Provisional Application No. 60/880,000, filed on Jan. 11, 2007. Application Ser. No. 12/008,509 is a continuation in part of U.S. application Ser. No. 10/691,823, filed Oct. 23, 2003, now U.S. Pat. No. 7,520,863, issued Apr. 21, 2009, which is a continuation-in-part of U.S. application Ser. No. 10/224,168, filed Aug. 20, 2002, now U.S. Pat. No. 7,128,718 issued Oct. 31, 2006, which claims priority of U.S. Provisional Application No. 60/366,739 filed on Mar. 22, 2002.

BACKGROUND AND SUMMARY OF THE INVENTION

1. Technical Background

This invention relates to medical devices, and more specifically to rapid-exchange balloon catheters or stent delivery systems with improved shaft designs.

2. Discussion

Catheter systems are used in a variety of therapeutic applications, including many vascular treatments. Various types of catheters are available, such as balloon catheters for procedures such as angioplasty. Angioplasty can be used to treat vascular disease, in which blood vessels are partially or totally blocked or narrowed by a lesion or stenosis.

In many instances of vascular disease, a local area of a blood vessel may become narrowed. This narrowing is called a lesion or stenosis, and may take the form of hard plaque, cholesterol, fats, or viscous thrombus. Such a stenosis may cause heart attack or stroke, which are significant health problems affecting millions of people each year. Typical disease patterns involve stenosis development, causing a blockage or partial blockage at the site.

For example, various procedures are well known for addressing stenoses and opening body vessels that have a constriction due to plaque buildup or thrombus, etc. With such procedures, an expansive force may be applied to the lumen of the stenosis. This outward pressing of a constriction or narrowing at the desired site in a body passage is intended to partially or completely re-open or dilate that body passageway or lumen, increasing its inner diameter or cross-sectional area. In the case of a blood vessel, this procedure is referred to as angioplasty. The objective of this procedure is to increase the inner diameter or cross-sectional area of the vessel passage or lumen through which blood flows, to encourage greater blood flow through the newly expanded vessel.

Often, it is deemed to be desirable to leave a device in place at the site of the expanded lumen of the stenosis, to provide support for the vessel wall at that location. Such a device may provide a scaffold type of structure about which, for example, endothelium development can occur to help repair the diseased, injured or damaged area. This scaffold device is referred to as a stent or endoprosthesis, and may have various designs, often having a resilient, flexible and cylindrical spring shape. In some cases, the stent which is a flexible cylinder or scaffold made of metal or polymers may be permanently implanted into the vessel. The stent tends to hold the lumen open longer, to reinforce the vessel wall and improve blood flow.

Stenting has come to be an accepted interventional medical procedure in many situations where vessels require support on a long-term basis. In operation, a catheter is used to transport the stent into and through a blood vessel, until the stent or the like is positioned at a desired location. Once at the desired location, the stent is deployed to provide internal support of the vessel or other treatment.

Some stents are deployed by an angioplasty balloon catheter, either during the angioplasty procedure or after a balloon has opened up the stenosis. These are called balloon-deployed or balloon-expandable stents. The balloon-expandable stents are forcibly expanded by a balloon or similar device through plastic deformation of the stent from a smaller to a larger diameter.

According to some aspects of the present invention, a balloon catheter or stent delivery system may have a rapid-exchange configuration, and an improved catheter shaft with a hypotube having a cut pattern portion that extends from the hub to a point at or near the balloon.

As an example, the present invention will be described in relation to coronary, peripheral, and neurological vascular treatments using a rapid-exchange balloon catheter or stent delivery system. However, it should be understood that the present invention relates to any rapid-exchange catheter system having the features of the present invention, and is not limited to a particular type of catheter, with or without a stent, or the location or type of treatment.

Some catheters have a relatively long and flexible tubular shaft defining one or more passages or lumens, and may deliver and deploy the stent near one end of the shaft. This end of the catheter where the balloon is located is customarily referred to as the "distal" end, while the other end is called the "proximal" end. The proximal end of the shaft may lead to a hub coupling for connecting the shaft and the lumen(s) to various equipment.

A common treatment method for using such a catheter is to advance the catheter into the body of a patient, by directing the catheter distal end percutaneously through an incision and along a body passage such as a blood vessel until the balloon is located within the desired site. The term "desired site" refers to the location in the patient's body currently selected for treatment by a health care professional. After the balloon is inflated and/or a stent is deployed within the desired site, it will tend to expand to press outward on the body passage.

Catheter systems are often designed for the smallest possible outer diameter or profile, particularly at the distal end. This small profile may be preferred for access into small vessels, either following angioplasty or during a procedure called "direct stenting" where no angioplasty is performed.

Many catheter systems are used with a flexible guidewire. The guidewire is often metal, and is slidably inserted along the desired body passage. The catheter system is then advanced over the guidewire by "back-loading" or inserting the proximal end of the guidewire into a distal guidewire port leading to a guidewire lumen defined by the catheter system. Such a guidewire lumen may extend along the entire length or only part of the catheter.

The catheter systems with a full-length guidewire lumen are described as "over-the-wire" catheters, in that the guidewires resides inside a catheter lumen throughout the length of the catheter. Over-the-wire catheter systems provide some advantages, including improved trackability, preventing prolapse of the guidewire, the ability to flush the guidewire lumen while the catheter is in the patient, and the capability of easily removing and exchanging the guidewire while retaining the catheter in a desired position in the patient.

In some circumstances it may be desirable to provide a "rapid-exchange" catheter system, which offers the ability to easily remove and exchange the catheter while retaining the guidewire in a desired position within the patient. In the balloon catheter arena, rapid-exchange balloon catheters are disclosed in U.S. Pat. Nos. 5,380,283 and 5,334,147 issued to Johnson on Jan. 10, 1995 and Aug. 2, 1994, both entitled "Rapid-Exchange Type Dilatation Catheter." Also, U.S. Pat. No. 5,531,690 issued to Solar on Jul. 2, 1996, entitled "Rapid-Exchange Catheter" describes a rapid-exchange balloon catheter, as does U.S. Pat. No. Re. 36,104 to Solar entitled "Dilation Catheter With Eccentric Balloon."

In other words, rapid-exchange balloon dilatation catheters are capable of advancement into the vascular system of a patient along a pre-positioned guidewire, for balloon angioplasty or a similar procedure. The guidewire occupies a catheter lumen extending only through a distal portion of the catheter. With respect to the remaining proximal catheter portion, the guidewire exits the internal catheter lumen through a proximal guidewire port, and extends in parallel along the outside of the catheter proximal portion. Of course, the entire catheter and guidewire assembly is typically contained within the lumen of a guiding catheter, which surrounds and guides the balloon catheter or stent delivery system to the desired site.

Because a majority of the guidewire is outside the catheter shaft, it may be manually held in place as the catheter is removed. Because the distal catheter guidewire lumen is shorter than the guidewire length that remains outside the patient, the catheter may be removed while also holding the guidewire, until the guidewire may be grasped at a point distal of the catheter. Completing a catheter exchange simply requires reversing the removal process. This rapid-exchange technique enables a single physician to exchange balloon catheters, without requiring a guidewire extension to temporarily double the guidewire length.

It is desirable to provide a balloon catheter having an optimum combination of various performance characteristics, which may be selected among: flexibility, lubricity, pushability, trackability, crossability, low profile, pull strength, inflation/deflation times, inflation pressures, and others. Flexibility may relate to bending stiffness of a medical device (balloon catheter and/or stent, for example) in a particular region or over its entire length, or may relate to the material hardness of the components. Lubricity may refer to reducing friction by using low-friction materials or coatings. Pushability may relate to the column strength of a device or system along a selected path. Trackability may refer to a capability of a device to successfully follow a desired path, for example without prolapse. Crossability may be clarified by understanding that physicians prefer to reach the desired site with the balloon catheter while encountering little or no friction or resistance. Profile may refer to a maximum lateral dimension of the balloon catheter, at any point along its length.

The balloon catheter of the present invention provides various advantages, which may include: pushability, optimized flexibility along the catheter length, torsional strength, pull strength, low profile, etc. Some embodiments of the present invention may also provide additional benefits, including smooth transitions in flexibility, lubricious guidewire lumen, etc.

Structurally, catheters may have a flexible shaft extending between a proximal end and a distal end, and define one or more tubular passages or "lumens" extending through part or all of the catheter shaft. Such lumens often have one or more openings, referred to as "ports."

When a lumen is adapted to slidingly receive a guidewire, it is referred to as a "guidewire lumen," and it will generally have a proximal and distal "guidewire port." The distal guidewire port is often at or near the catheter shaft distal end.

A hub is often affixed to the catheter shaft proximal end. The hub may serve a variety of functions, including providing a handle for manipulating the catheter, and/or defining proximal port(s) communicating with lumen(s) defined by the catheter shaft. When the catheter has a guidewire lumen, a proximal guidewire port may be located at some point along the sidewall of the catheter shaft, or a hub may define the proximal guidewire port.

A guidewire has a flexible wire-like structure extending from a proximal end to a distal end. The guidewire will usually be of a size selected to fit into and slide within a corresponding guidewire lumen of a catheter.

The terms "tube" and "tubular" are used in their broadest sense, to encompass any structure arranged at a radial distance around a longitudinal axis. Accordingly, the terms "tube" and "tubular" include any structure that (i) is cylindrical or not, such as for example an elliptical or polygonal cross-section, or any other regular or irregular cross-section; (ii) has a different or changing cross-section along its length; (iii) is arranged around a straight, curving, bent or discontinuous longitudinal axis; (iv) has an imperforate surface, or a periodic or other perforate, irregular or gapped surface or cross-section; (v) is spaced uniformly or irregularly, including being spaced varying radial distances from the longitudinal axis; or (vi) has any desired combination of length or cross-sectional size.

Any suitable additional material may also be used to make catheters and hubs as described, including polymers and other materials suitable for use with medical devices.

It is of course possible to build various kinds and designs of catheters according to the present invention, by various techniques and of various materials, to obtain the desired features. It should be noted that the present invention also relates to methods for making and using medical devices, during or in preparation for medical treatment of a patient.

These and various other objects, advantages and features of the invention will become apparent from the following description and claims, when considered in conjunction with the appended drawings. The invention will be explained in greater detail below with reference to the attached drawings of a number of examples of embodiments of the present invention.

BRIEF DESCRIPTION OF THE DRAWINGS

FIGS. 14 and 15 are partial cross-section views of catheter shaft components, in the region of a proximal guidewire port;

FIG. 16 is a transverse cross-section view of catheter shaft components, in another possible embodiment;

FIGS. 17-18 are partial views of catheter shaft components, in particular inner tubular bodies;

FIGS. 19-20 are partial side elevation views of a balloon catheter and stent, alternatively showing a deflated crimped state, and an inflated deployment state.

DETAILED DESCRIPTION OF THE PREFERRED EMBODIMENTS

Figure 1:
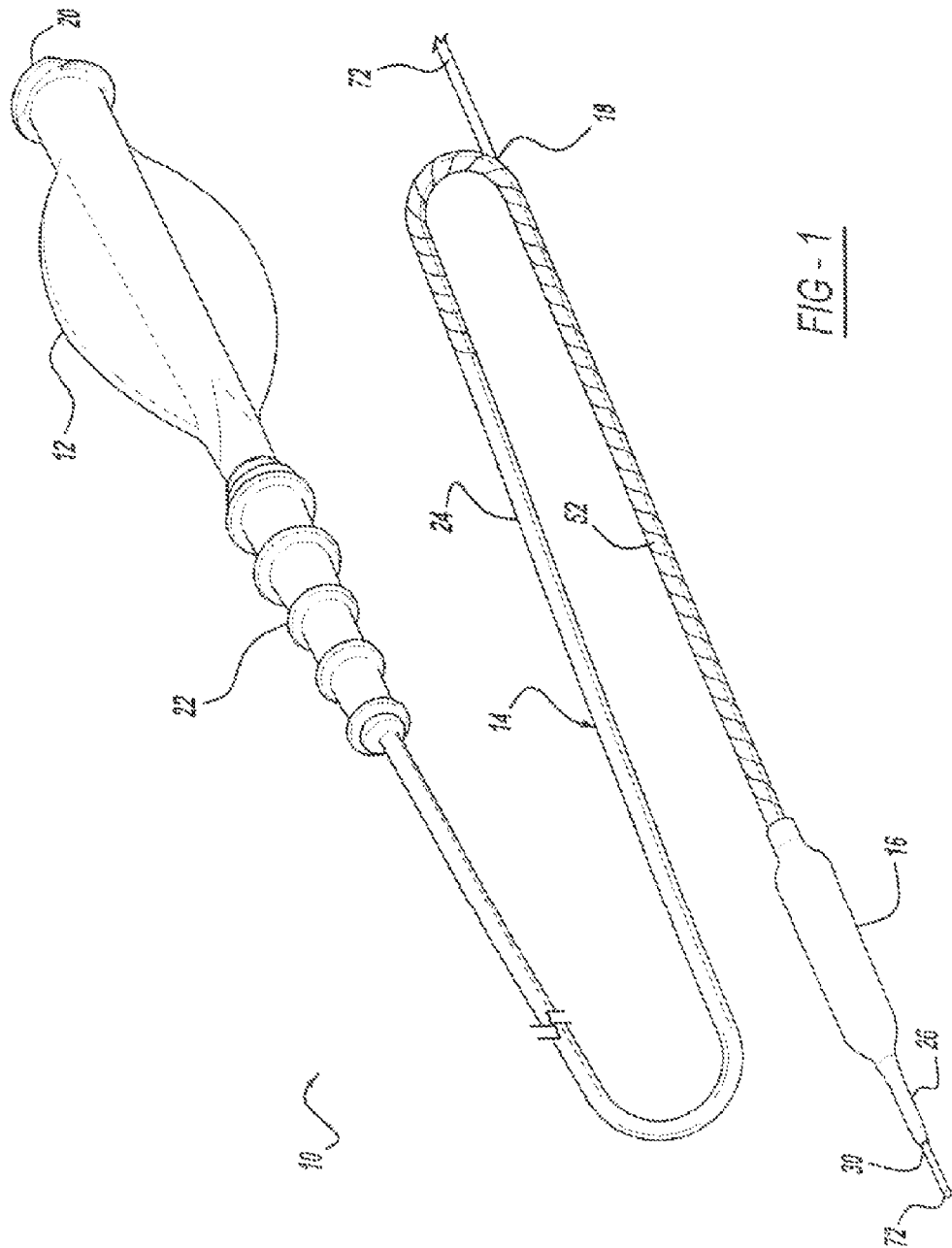
FIG. 1 is a perspective view of a balloon catheter with a rapid-exchange configuration.
Figure 2:
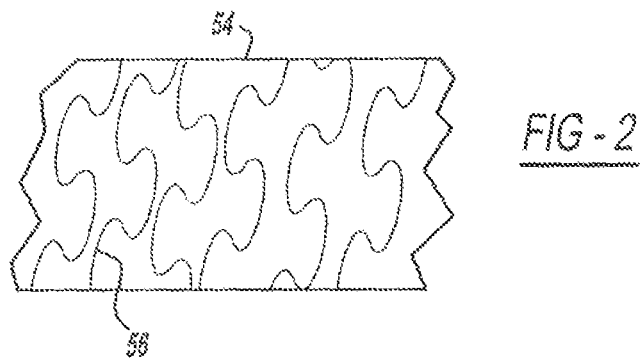
FIG. 2 is a partial side elevation view of a catheter shaft component having an undulating helical cut pattern.
Figure 3:
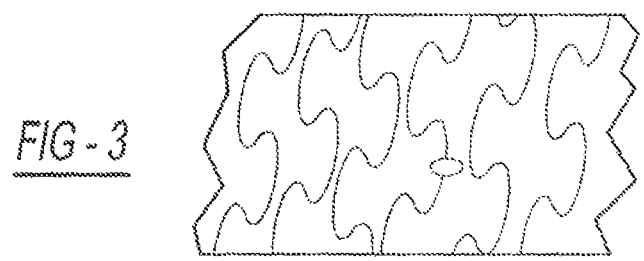
FIGS. 3-8 are partial side elevation views of catheter shaft components with an undulating helical cut pattern, showing various positions and shapes for a guidewire port.
Figure 4:
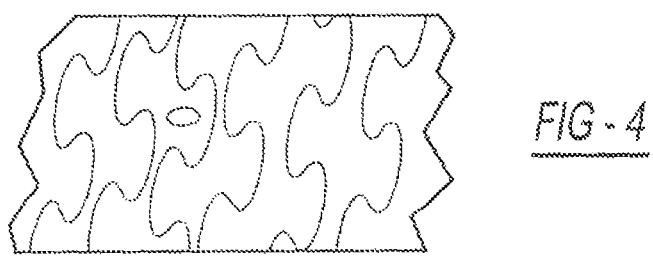
Figure 5:
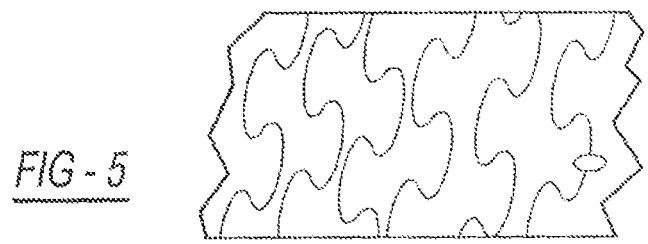
Figure 6:
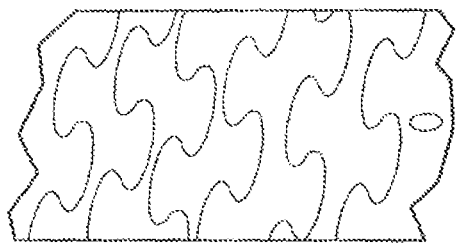

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, a balloon catheter and stent delivery system are depicted, with an embodiment of the present invention being shown generally at 10. The illustrated balloon catheter and stent delivery system of course illustrate only some of many different designs within the scope of the present invention.

FIG. 1 shows an embodiment of the present invention, and includes a proximal hub 12, a flexible catheter shaft 14, and a balloon 16. An intermediate portion of the shaft defines a proximal guidewire port 18. The proximal hub 12 preferably provides an operating handle for a physician, and an inflation port 20. A tubular strain relief 22 bridges the transition between the proximal hub 12 and the flexible shaft 14.

At least a distal portion of the catheter shaft 14 has a coaxial arrangement, including a tubular outer body 24 surrounding at least a portion of a tubular inner body 26. The inner body 26 defines a guidewire lumen 28 having a lumen diameter, extending from a distal guidewire port 30 defined at the distal tip of the inner body 26 to the proximal guidewire port 18. Guidewire lumen 28 can slidingly accept a guidewire 72. An inflation lumen 32 is defined by the annular space between the outer body 24 and inner body 26, extending from the proximal inflation port 20 to the balloon interior.

The balloon catheter shown in the drawings has what is referred to as a rapid-exchange configuration, in which the guidewire lumen extends from a distal guidewire port to a proximal port located at some intermediate position between the balloon and the proximal hub.

The present invention provides a novel improved shaft design having an optimized bundle of performance characteristics, including pull strength, column strength, a relatively smooth flexibility curve along the length of the catheter, and distal tip flexibility, minimum deflated outer profile, maximum guidewire lumen inner diameter, and hoop strength of the tubular inner body, and maximum flexibility at the distal tip.

Accordingly, the illustrated balloon catheter preferably has a hypotube 48 extending from the proximal end of the catheter shaft to a point at or near the balloon proximal leg. Hypotube 48 has a cut pattern extending from a position proximal of the proximal guidewire port, to a position at or near the balloon proximal leg (which is also at or near the distal end of the hypotube 48). This hypotube 48 and cut pattern assist in crossing tight lesions, and enhance the flexibility of the entire distal portion of the catheter 10.

The catheter has a shaft with proximal and distal ends, extending between a balloon near the distal end and a hub at the proximal end. The shaft defines an inflation lumen extending from a proximal inflation port defined by the hub to the balloon interior, and a guidewire lumen extending from a proximal guidewire port at an intermediate position of the shaft to a distal guidewire port at the catheter distal end. Accordingly, the catheter has a "rapid-exchange" configuration.

The catheter shaft, sometimes called the chassis, includes a hypotube 48, which extends from the proximal hub 12 to a position near the proximal seal of the balloon 16. The hypotube may be made of stainless steel or a "super-elastic" or "shape memory" metal such as nitinol, or any other suitably strong material. The hypotube 48 has a cut pattern over a portion of its distal length. This cut pattern may be laser-cut, or formed by any other suitable technique. The introduction of this flexibility/stiffening profile will eliminate any need for a separate stiffening wire/ribbon, or a skive on the distal portion of the hypotube.

Figure 7:
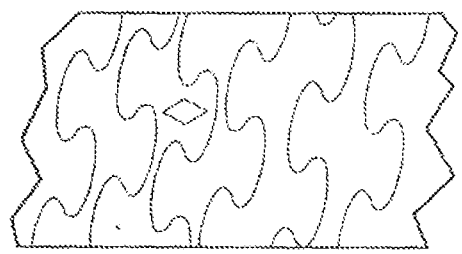
Figure 8:
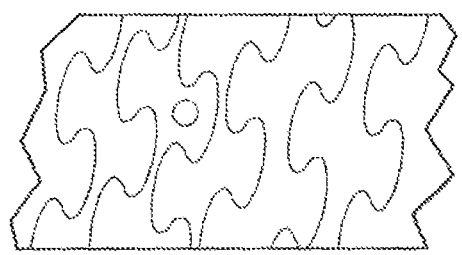
Figure 9:
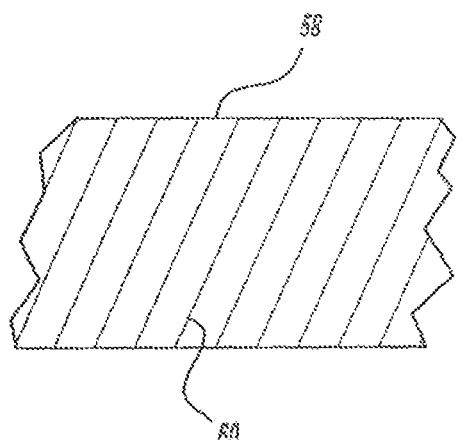
FIG. 9 is a partial side elevation view of a catheter shaft component with a spiral cut pattern.
Figure 10:
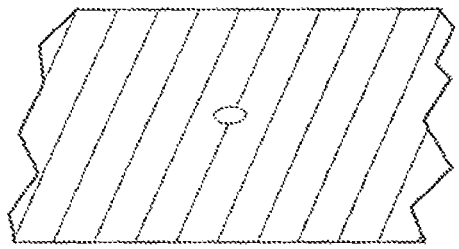
FIGS. 10-13 are partial side elevation views of catheter shaft components with a spiral cut pattern, showing various positions for a guidewire port.
Figure 11:
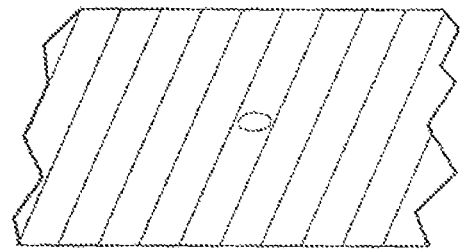
Figure 12:
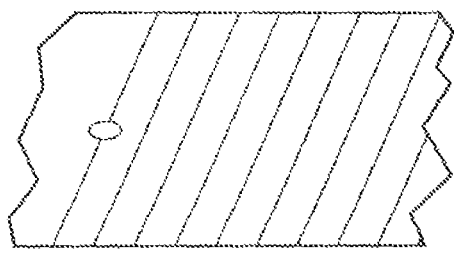
Figure 13:
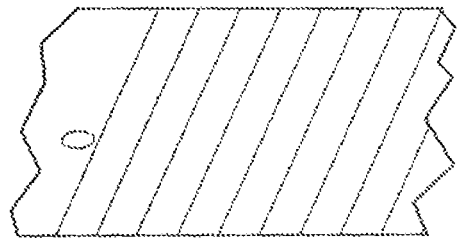

The cut pattern may be a variable pitch complex spiral configuration, as shown in FIGS. 2-8, which may be both stretch resistant and compression resistant, allowing for better load transfer along the shaft length and permitting the system to transmit torque. The proximal guidewire port may be positioned in various locations on the hypotube 54 relative to the cut pattern 56, as shown in FIGS. 3-8. As shown in FIGS. 7 and 8, the proximal guidewire port may have various shapes, including any suitable shape configuration, but in any event large enough to accommodate the outer diameter of the inner body. As shown in FIGS. 17 and 18, the proximal end of the inner body may be flared or segmented.

Of course, the hypotube 58 may have a regular spiral cut pattern 60 as shown in FIGS. 9-13 (rather than a complex one) with the proximal guidewire port being in various locations, as shown in FIGS. 10-13.

A heat-shrink polymer or other fluid-tight layer or coating is placed over at least the length of the profiled hypotube in the cut pattern region, excluding the rapid-exchange port, and serves as a fluid-tight seal for the inflation lumen. This material also serves as a bonding substrate for the proximal balloon seal, and may be a tie layer for an optional hydrophilic coating.

The guidewire lumen may have an inner body including a lumen with a low friction inner surface (for example, HDPE, PTFE, FEP, or PD-Slick) and a polymer outer surface that will allow securement of the balloon seal. As shown in FIG. 16, the inner body may have a reinforcement configuration, which may include a metal coil or braid.

The inner body may anywhere in the region of the distal balloon leg seal. The outer layer and reinforcement (or the outer layer alone) distal of the balloon may be removed prior to the addition of additional tip material. An additional polymer material may be placed over the inner body just distal to the distal seal. Another alternative is to butt-fuse polymer material to the distal end of the inner body. The tip may be tapered to decrease profile or may remain square, and may be of lengths from 0-1 cm.

The rapid-exchange port for the design may exit through the hypotube wall, however it may also exit distal to the profiled hypotube. The port may be cut into the hypotube at an angle (for example, 15-90°) to the longitudinal axis of the shaft, and may be located on the circumferential cut pattern, between the rings of the pattern, on the un-cut portion, or at the proximal onset of the cut pattern.

The hypotube may be indented to allow for ease of entry of the guidewire, as shown in FIG. 16. The proximal end of the inner body may exit the port and be bonded onto the outer body jacket. An extension of non-reinforced polymer tubing may be added to the proximal end to assist in bonding. The end may be square cut or angle cut, then flared and cut into segments along the circumference. Heat-shrink or other polymer materials may be used as a process aid or as a permanent material on the device.

Bonding of the tip and balloon seals may be achieved by heating dies, RF bonding, or laser bonding. If the latter is chosen as the preferred process, the method employed may use a dichroic multi-wavelength source for wavelength specific materials. The intent would be for one wavelength to heat the metal hypotube or mandrel beneath both polymers (tip to inner body, balloon to shaft, or balloon to inner body) and induct heat to indirectly melt polymers. The second wavelength will interact with the heat shrink to force the materials together and direct flow.

Extension of the hypotube component more distally will eliminate the need for a separate stiffening wire along the shaft length, and will permit better transfer of load from the proximal hub to the tip of the delivery system. Eliminating or minimizing sharp transitions from the solid hypotube to the polymer distal section will help to minimize or prevent shaft kinking while also permitting better load transfer.

The hypotube adds strength to the design, holding its shape under pressure and bending. This will improve inflation/deflation by resisting outer body ovalization in tight or tortuous vessels.

Torquing the system can be achieved more effectively, as the load will be transmitted through the hypotube component. This will help overcome any static friction between the system and a guide catheter and/or vessel walls.

The interlocking cut pattern will make the system more resistant to stretching or kinking when either advancing or retracting the system.

A reinforced inner body will minimize or eliminate guidewire lumen ovalization, which will subsequently minimize or eliminate stent delivery system/guidewire friction interactions.

Figure 21:
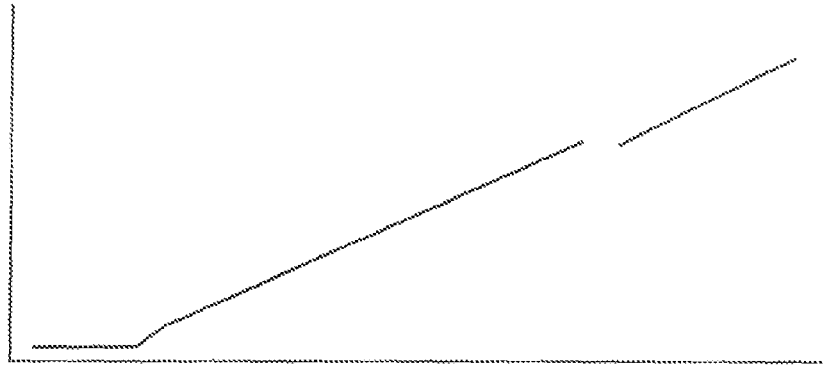
FIGS. 21-22 are graphical representations of possible arrangements of the helical angles of a cut pattern, along the length of a hypotube catheter component.
Figure 22:
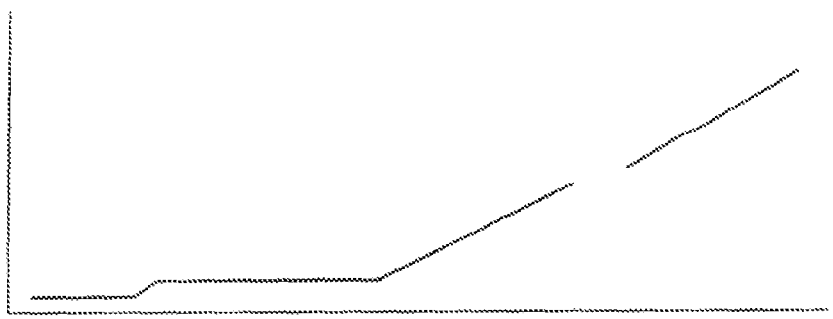

Various modifications are possible, such as positioning the rapid-exchange port at any location along the shaft length where practical for it to function as a rapid exchange system. The cut pattern may have various shapes, and may define a constant helical angle or variable angles as shown in FIGS. 21 and 22. Also, as shown in FIGS. 7 and 8, the shape of the rapid-exchange port may vary. For example, it may be oval, diamond, circular, asymmetric, or oblong.

If the rapid-exchange port is not located on the hypotube, the rapid-exchange port may be at the end of or distal to the hypotube, which may or may not include a cut profile. The hypotube may be attached to an outer body tube with or without a transition tube. The outer body and transition tube may be reinforced with a coil or braid, with flat or round wires of metallic materials such as stainless steel or nitinol. The hypotube may be indented at the port to allow for ease of entry of the guidewire.

The outer body polymer jacket may have a single or variable durometer, depending on the desired performance characteristics trying to be achieved.

The cut pattern may have a variable pitch profile with gradual transition(s) or a stepped profile with abrupt transition(s), depending on the desired performance characteristics. The specific dimensions of the cut pattern may be varied to influence the performance characteristics of the hypotube shaft.

The guidewire lumen inner body may be made of different materials, depending on the desired performance characteristics (e.g. PTFE, FEP, HDPE, or PD Slick). The outer layer of this component may use single or multiple durometer materials. These materials will serve as the bonding surface for the distal balloon joint.

The PPI (pics per inch) for the braid or WPI (wraps per inch) for the coil will either be constant throughout the entire length of the lumen, or varied to give specific performance characteristics at discrete locations along the length.

The balloon 16 preferably has a central cylindrical working portion 34, proximal and distal tapering portions 36 and 38, and proximal and distal legs 40 and 42. The balloon proximal leg 40 is affixed to a distal end of the outer body 24 by any suitable method, including heat-sealing or adhesives. Likewise, the balloon distal leg 42 is directly or indirectly affixed to the inner body 26 near its distal end by any suitable method. Various tip configuration are also possible, including a soft tip component may be inserted between the distal balloon leg and the inner body. The positions of the proximal and distal ends of the balloon cylindrical working portion 34 may be indicated under fluoroscopy by a pair of proximal and distal radiopaque marker bands 44 and 46 affixed to the inner body 26.

The balloon 16 and stent 50 are shown in FIGS. 19 and 20, in a deflated state and an inflated state, respectively.

Various different materials may be used for the various components of a balloon catheter according to the present invention. Most of the balloon catheter components should preferably be made of materials having acceptable properties including biocompatibility, pull strength, longitudinal or column strength, and bending flexibility. Some of the preferred materials may include various plastics, referred to as polymers, including nylon, polyethylenes, polyurethanes, or PET. For example, the guidewire is preferably made of metal such as stainless steel, while the balloon 16 is preferably made of nylon. The components of the catheter shaft, including the inner and outer bodies 26 and 24, may be made of nylon, or a coextrusion of nylon and another polymer. Various radiopaque materials are available for the markers, including gold, iridium and platinum.

The present invention may of course be made with any suitable selection of dimensions and sizes.

Catheter manufacturing techniques are generally known in the art, including extrusion and coextrusion, coating, adhesives, and molding. The scope of the present invention encompasses the full extent of the claims, regardless of specific materials, numbers or other details present in this description of the preferred embodiments.

One of the many possible methods of making an angioplasty balloon catheter for performing a therapeutic procedure on a patient according to the principles of the present invention includes the steps of forming a tubular inner body, a tubular outer body, and forming an angioplasty balloon using known techniques, including extrusion. The inner and outer bodies, and the balloon all define proximal and distal ends. Then, a radiopaque marker is affixed to the tubular inner body, and a mandrel is inserted within a lumen defined by the tubular inner body. The inner body and mandrel assembly is inserted into the balloon, and the outer body is inserted within the balloon proximal leg. The balloon proximal leg is heat-sealed to the outer body, and then the distal leg of the balloon is heat-sealed to the inner body at a position distal of the wall thickness transition.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A stent delivery system having a proximal end and a distal end, comprising:
   a hypotube with a proximal and distal end and having a continuous cut formed therein, the cut having a variable pitch complex spiral configuration with respect to a longitudinal axis of the hypotube;
   a balloon defining an interior;
   a hub defining a proximal inflation port; and
   a flexible shaft having a proximal and distal end; the shaft extending between the balloon and hub; the hub being affixed to the proximal end of the flexible shaft, and the balloon being affixed to the flexible shaft at or near its distal end; the flexible shaft defining an inflation lumen extending from the proximal inflation port to the interior of the balloon, the flexible shaft defining a distal guidewire port at or near the distal end of the catheter and a proximal guidewire port positioned between the hub and balloon, the flexible shaft defining a guidewire lumen extending between the proximal and distal guidewire ports;
   at least a portion of the shaft including an inner tubular body and an outer tubular body, each having a proximal and distal end; the outer body surrounding at least a portion of the inner body;
   wherein the outer body includes the hypotube, and wherein the hypotube has a proximal and distal end, and extends from the proximal end of the shaft to a point at or near where the balloon is affixed to the flexible shaft, and the continuous cut provides a flexibility transition from a proximal portion to a distal portion of the outer body.

2. The stent delivery system of claim 1, wherein the continuous cut is over a portion of a distal length of the hypotube.

3. The stent delivery system of claim 1 comprising a rapid-exchange catheter.

4. The stent delivery system of claim 1, wherein the flexibility transition excludes a separate wire ribbon structure.

5. The stent delivery system of claim 1, wherein the flexibility transition excludes a skive on a distal portion of the hypotube.

6. The stent delivery system of claim 1, further comprising a fluid-tight outer layer surrounding at least the portion of the hypotube with the continuous cut.

7. A stent delivery system comprising:
   a flexible shaft with an interlocking cut pattern along a portion of its length;
   a balloon defining an interior;
   a hub defining a proximal inflation port;
   wherein the flexible shaft has a proximal and distal end; the shaft extending between the balloon and hub; the hub being affixed to the proximal end of the flexible shaft, and the balloon being affixed to the flexible shaft at or near its distal end; the flexible shaft defining an inflation lumen extending from the proximal inflation port to the interior of the balloon, the flexible shaft defining a distal guidewire port at or near the distal end of the catheter and a proximal guidewire port positioned between the hub and balloon, the flexible shaft defining a guidewire lumen extending between the proximal and distal guidewire ports;
   at least a portion of the shaft including an inner tubular body and an outer tubular body, each having a proximal and distal end; the outer body surrounding at least a portion of the inner body;
   wherein the outer body has a hypotube, and wherein the hypotube has a proximal and distal end, and extends from the proximal end of the shaft to a point at or near where the balloon is affixed to the flexible shaft, and the interlocking cut pattern provides a flexibility transition from a proximal portion to a distal portion of the outer body.

8. The stent delivery system of claim 7, wherein the interlocking cut pattern is over a portion of a distal length of the hypotube.

9. The stent delivery system of claim 7 comprising a rapid-exchange catheter.

10. The stent delivery system of claim 7 comprising a balloon catheter.

11. The stent delivery system of claim 7, further comprising a fluid-tight outer layer surrounding at least portion of the flexible shaft with the interlocking cut pattern.

12. The stent delivery system of claim 7, wherein the interlocking cut pattern is a repeating pattern.

13. The stent delivery system of claim 7, wherein the flexibility transition excludes a separate wire ribbon structure.

14. The stent delivery system of claim 7, wherein the flexibility transition excludes a skive on a distal portion of the outer body.

* * * * *